United States Patent
Hutter (10) Patent No.: US 10,732,093 B2
(45) Date of Patent: Aug. 4, 2020

(54) GAS SENSOR

(71) Applicant: SENSORHUT LTD., Cambridge, Cambridgeshire (GB)

(72) Inventor: Tanya Hutter, Cambridge (GB)

(73) Assignee: SENSORHUT LTD. (GB)

(*) Notice: Subject to any disclaimer, the term of this patent is extended or adjusted under 35 U.S.C. 154(b) by 0 days.

(21) Appl. No.: 16/106,640

(22) Filed: Aug. 21, 2018

(65) Prior Publication Data
US 2018/0372613 A1 Dec. 27, 2018

Related U.S. Application Data

(62) Division of application No. 15/308,164, filed as application No. PCT/GB2015/051244 on Apr. 29, 2015.

(30) Foreign Application Priority Data

May 2, 2014 (GB) .................................. 1407770.5

(51) Int. Cl.
*G01N 15/14* (2006.01)
*G01N 33/497* (2006.01)
(Continued)

(52) U.S. Cl.
CPC ......... *G01N 15/1434* (2013.01); *G01N 21/31* (2013.01); *G01N 21/552* (2013.01);
(Continued)

(58) Field of Classification Search
CPC ........... G01N 2021/7713; G01N 21/65; G01N 15/1434; G01N 2015/0065;
(Continued)

(56) References Cited

U.S. PATENT DOCUMENTS 5,071,248 A 12/1991 Tiefenthaler et al.
5,268,972 A 12/1993 Tabacco et al.
(Continued)

FOREIGN PATENT DOCUMENTS

CA 2270276 A1 10/2000
EP 0072627 A2 12/1983
(Continued)

OTHER PUBLICATIONS

L. De Stefano et al., "Optical sensors for vapors, liquids, and biological molecules based on porous silicon technology," in IEEE Transactions on Nanotechnology, vol. 3, No. 1, pp. 49-54, Mar. 2004. doi: 10.1109/TNANO.2004.824019 (Year: 2004).*
(Continued)

*Primary Examiner* — Violeta A Prieto
(74) *Attorney, Agent, or Firm* — Tarolli, Sundheim, Covell & Tummino LLP (57) ABSTRACT

We describe a method of selectively detecting the presence of an analyte, the method comprising: providing at least one waveguide, the waveguide having a core comprising porous material; absorbing an analyte sample into said porous material of said core such that said analyte sample is held within pores of said core; waveguiding radiation along said at least one waveguide to an output to provide output radiation; measuring one or more spectral features of said output radiation due to absorption or scattering of said waveguided radiation by said absorbed analyte sample; selectively identifying the presence of a target analyte in said analyte sample from said one or more spectral features. In embodiments spectral features are measured for multiple different waveguide core regions having different physical/chemical properties modified to provide additional selectivity to the target analyte(s), and these measurements combined to identify the target analyte.

13 Claims, 9 Drawing Sheets

(51) Int. Cl.

| | |
|---|---|
| *G01N 21/31* | (2006.01) |
| *G01N 21/552* | (2014.01) |
| *G01N 21/65* | (2006.01) |
| *G01N 21/77* | (2006.01) |
| *G02B 6/122* | (2006.01) |
| *B82Y 20/00* | (2011.01) |
| *G01N 15/00* | (2006.01) |
| *G01N 21/03* | (2006.01) |
| *G01N 21/25* | (2006.01) |
| *G01N 21/85* | (2006.01) |

(52) U.S. Cl.
CPC ......... *G01N 21/65* (2013.01); *G01N 21/7703* (2013.01); *G01N 33/497* (2013.01); *G02B 6/1225* (2013.01); *B82Y 20/00* (2013.01); *G01N 21/253* (2013.01); *G01N 2015/0065* (2013.01); *G01N 2021/0346* (2013.01); *G01N 2021/7713* (2013.01); *G01N 2021/7783* (2013.01); *G01N 2021/8542* (2013.01); *G01N 2033/4975* (2013.01); *G01N 2201/08* (2013.01)

(58) Field of Classification Search
CPC ... G01N 2021/0346; G01N 2021/7783; G01N 2021/8542; G01N 2033/4975; G01N 21/253; G01N 21/31; G01N 21/552; G01N 21/7703; G01N 2201/08; G01N 33/497; G01N 21/3504; G01N 21/3577; G01N 21/77; B82Y 20/00; G02B 6/1225
See application file for complete search history.

(56) References Cited

U.S. PATENT DOCUMENTS

| | | |
|---|---|---|
| 6,375,725 B1 | 4/2002 | Bernard et al. |
| 7,343,074 B1 | 3/2008 | Gallagher et al. |
| 8,617,471 B2 | 12/2013 | Chakravarty et al. |
| 8,636,955 B2 | 1/2014 | Chakravarty et al. |
| 9,013,707 B2 | 4/2015 | Ruschin et al. |
| 2002/0191884 A1 | 12/2002 | Letant et al. |
| 2007/0035819 A1 | 2/2007 | Bahatt et al. |
| 2008/0205837 A1 | 8/2008 | Gallagher et al. |
| 2008/0297799 A1 | 12/2008 | Caron et al. |
| 2009/0059234 A1 | 3/2009 | Dreyer et al. |
| 2010/0098592 A1 | 4/2010 | Rong et al. |
| 2011/0128537 A1 | 6/2011 | Bond et al. |
| 2011/0266161 A1 | 11/2011 | Tao et al. |
| 2012/0013911 A1 | 1/2012 | Ruschin et al. |
| 2012/0327398 A1 | 12/2012 | Chakravarty et al. |
| 2013/0081447 A1 | 4/2013 | Carter et al. |
| 2013/0114082 A1 | 5/2013 | Sailor et al. |

FOREIGN PATENT DOCUMENTS

| | | |
|---|---|---|
| EP | 0979994 A2 | 2/2000 |
| EP | 2108944 A2 | 10/2009 |
| EP | 2115428 A2 | 11/2009 |
| FR | 2856150 A1 | 12/2004 |
| JP | 2011075513 A | 4/2011 |
| WO | 01/94915 A1 | 12/2001 |
| WO | 201107868 A1 | 9/2011 |
| WO | 2011140156 A2 | 11/2011 |

OTHER PUBLICATIONS

Tinsley-Bown et al., "Tuning the Pore Size and Surface Chemistry of Porous Silicon for Immunoassays," phys. stat. sol. (a), 182: 547-553 (2000). doi:10.1002/1521-396X(200011)182:1<547::AID-PSSA547>3.0.CO;2-C (Year: 2000).*
Final Office Action for U.S. Appl. No. 15/308,164 dated Dec. 12, 2019.
International Search Report for Application No. PCT/GB2015/051244 dated Sep. 3, 2015.
Charrier, Joël, et al. "Structural and optical studies of porous silicon buried waveguides: Effects of oxidation and pore filling using DR1 dyes." Optical Materials 30.3 (2007): 431-437.
Search Report for corresponding UK application No. GB1407770.5 dated Nov. 18, 2014.
Hutter, T. et al; "Theoretical study of porous silicon waveguides and their applicability for vapour sensing", Proc. COMSOL conference Paris, 2010.
Hutter, et al., "Dynamic Range Enhancement and Phase-Ambiguity Elimination in Wavelegnth-Interrogated Interferometric Sensor", Sensors and Actuators B: Chemical 178 (2013) 593-597.
Haji, et al., "Anti Resonant Reflecting Optical Waveguide Structure Based on Oxidezed Porous Silicon for Label Free Bio Sensing Applications", Applied Physics Letters 100, 111102(2012), 2012 American Institute of Physics.

* cited by examiner

GAS SENSOR

RELATED APPLICATIONS

The present invention is a Divisional application claiming priority to U.S. application Ser. No. 15/308,164, filed on 1 Nov. 2016; which claims priority to International Application No. PCT/GB2015/051244, filed on 29 Apr. 2015; which claims priority from GB 1407770.5, filed 2 May 2014, the entirety of each of which is incorporated herein by reference.

FIELD OF THE INVENTION

This invention relates to methods and apparatus for selectively detecting the presence of an analyte, in particular a gas (vapour), and to methods of fabricating sensors for such methods/apparatus.

BACKGROUND TO THE INVENTION

Many sensors based on porous silicon have been reported, and some use porous silicon waveguides. In particular we have previously described sensors which measure the change in refractive index of a porous waveguide: Tanya Hutter, Nikos Bamiedakis and Stephen Elliott, "*Theoretical Study of Porous Silicon Waveguides and Their Applicability for Vapour Sensing*", Proceedings of the COMSOL Conference 2010 Paris, 2010; Tanya Hutter, Stephen R. Elliott and Shlomo Ruschin, Dynamic Range Enhancement and Phase-Ambiguity Elimination in Wavelength-Interrogated Interferometer Sensor, *Sensors and Actuators B*, 178, 593-597, 2013. Other work on porous silicon waveguides for biosensing can be found in L. Haji et al (2012). However these approaches rely on interference techniques to measure the change in refractive index of porous silicon, which limits their selectivity. By contrast, typical waveguide-based sensors provide the target material on an outer surface of the waveguide and rely on the interaction of an evanescent wave (of light propagating within the waveguide) with the analyte, which has limited sensitivity.

Other background prior art can be found in: EP0979994, EP2108944, US2012/0327398, U.S. Pat. No. 8,617,471, US2013/0081447, EP2108944, U.S. Pat. No. 8,636,955, WO2011/140156, WO2011/107868, JP2011/075513, EP2115428, US2009/059234, FR2856150, U.S. Pat. No. 6,375,725, and WO01/94915.

As noted, the above described techniques suffer from various problems including a lack of specificity and sensitivity.

SUMMARY OF THE INVENTION

According to the present invention there is therefore provided a method of selectively detecting the presence of an analyte, the method comprising: providing at least one waveguide, the waveguide having an optical core comprising porous material; absorbing an analyte sample into said porous material of said core such that said analyte sample is held within pores of said core; waveguiding radiation along said at least one waveguide to an output to provide output radiation; measuring one or more spectral features of said output radiation due to absorption or scattering of said waveguided radiation by said absorbed analyte sample; selectively identifying the presence of a target analyte in said analyte sample from said one or more spectral features.

In some preferred embodiments the radiation comprises optical radiation of any suitable wavelength or range of wavelengths including, but not limited to: ultraviolet, visible, near and far infrared; this may be delivered to the wave guide for example via a fibre optic. In principle, however, radiation of other wavelengths such as terahertz radiation may also be employed. By absorbing the analyte, typically a gas (vapour) into the porous material of the core the waveguide structure enables absorption spectroscopy to be performed on the analyte sample with a greater signal than is provided by other approaches. Thus in embodiments of the method the measured spectral features of the output radiation are due to one or more inherent properties of the absorbed analyte sample. In embodiments the porous material may contain substantially only the analysed material (and functionalising material, if used).

Preferably the absorption spectrum of the absorbed analyte is interrogated, but in principle other forms of spectroscopy such as scattering or Raman spectroscopy may additionally or alternatively be employed. Thus in embodiments the one or more spectral features identified by the method comprise features at absorption wavelength peaks/troughs of the analyte(s), or in principle features at scattering (Raman) peaks. The method may be used to selectively identify the presence of one or more target analytes, for example a mixture of gases. In embodiments the measuring of the one or more spectral features may simply comprise comparison with a threshold to identify whether or not a target analyte is present in the sample.

The use of a waveguide with a porous, at least partially exposed core provides additional opportunities for selective detection of one or more targets. (As the skilled person will know, the (optical) core of a waveguide is the region of the waveguide in which light propagates when travelling through the waveguide). Such an approach also enables selective exclusion of one or more chemical compounds from the core. In broad terms, the pore size of pores in the waveguide may be tuned to selectively exclude larger molecules. More generally, embodiments of the method employ a plurality of different core regions modified in different ways, either physically and/or chemically, to provide additional selectivity to the target analyte or analytes. The different core regions may be different parts of the same waveguide and/or may be parts of different waveguides—for example in embodiments an array of waveguides may be employed with a set of different pore sizes and/or surface modifications.

One difficulty with, for example, NIR spectroscopy is that it can be difficult to distinguish between certain different types of molecule. For example an OH absorption band is seen for both water and methanol; and in a long chain hydrocarbon or fatty acid it can be difficult to distinguish the length of the chain. In embodiments of the method, therefore, a set of different core regions is provided each with a different pore size distribution—that is with pore size distributions having peaks at different pore sizes. The pore size may be measured by any convenient technique; the skilled person will appreciate that depending upon the measurement technique (see later) what is being measured may not exactly correspond to a physical core dimension at a surface of the core of the waveguide. However in embodiments of the method the particular precise pore size may not be important provided that a set of different pore sizes is employed, providing some differentiation between one or more target molecules and the background. The skilled person will also appreciate that, broadly speaking, larger pores are associated with greater porosity (i.e. a greater percentage of unoccupied space in the porous 'sponge'), and thus porosity may be employed as a proxy for pore size in some situations.

Preferably the waveguide core comprises a mostly open pore network (internal pores have a pathway to the external core surface), rather than a mostly closed pore network, to facilitate absorption of the analyte, though this is not essential. (Pores produced in silicon by the electrochemical method described later are mostly open).

Additionally or alternatively one or more core regions of the one or more waveguides may be derivatized or functionalised, for example by treating the core material so that an internal surface of the pores is at least partially coated with a molecular material, in particular one which changes an affinity of the core waveguide material for the target analyte or analytes. Thus an internal surface of the pores may be provided with one or more different functional groups. The skilled person will be aware of many such functional groups which may be provided including, but not limited to: $CH_3$, CN, COOH, $NH_2$, and longer alkyl chains. The skilled person will also be aware of many such functionalising techniques including techniques based on small molecules, polymers, and self-assembled layers such as self-assembled monolayers (see, for example, U.S. Pat. No. 6,518,205, WO2002/079085, and WO2000/026019). Functionalising the pores in the core may additionally or alternatively comprise a physical treatment such as plasma treatment. Thus the waveguide core may be functionalised with a small molecule or polymer ligand, such as a hydrophilic or hydrophobic ligand, and/or a ligand having functional groups such as alcohol (—OH), aldehyde (—COH), amide (—CON), carboxylic acid (—COOH), methyl (—$CH_3$) or the like. A more complex functionalising material may also be employed, for example a biologically active molecule or peptide/protein such as DNA, RNA, or an antibody. For example these may be covalently coupled to a functionalised or native silicon/oxide surface.

Where multiple core regions with different properties are provided the multiple signals from such regions may be analysed using multi-component analysis, such as principle component analysis or one of the many similar techniques, to more accurately/selectively identify the presence of one or more targets.

Additionally or alternatively further selectivity/specificity may be achieved by operating at two or more different temperatures: both the physical and chemical interactions of a target with the porous core material are temperature dependent. Thus by operating at more than one temperature a further parameter is obtained which can be used to distinguish between targets and/or distinguish a target from the background. In broad terms, operating at multiple temperatures enables targets to be distinguished based upon their intrinsic properties in addition to their absorption spectrum. This can facilitate differentiating between, for example, long and short chain molecules. In a functionalised device binding of a target is temperature-dependent and changing temperature may be used for increased selectivity. In addition, the time dependent sensor signal (transient response) provides further discrimination between analytes.

More particularly, depending upon the temperature and other parameters such as pore size/shape, a target material may become liquid in the pores at certain vapour concentrations and certain temperatures. Thus the operating temperatures may be selected to change a degree of vapour condensation of the target within the pores. As well as providing additional selectivity depending upon the temperatures chosen, interrogating a condensed material in the gaseous and liquid phase generates different types of spectroscopic data—for example an absorption peak may vary in width. More generally, however, the temperature change may simply change the degree of analyte adsorption by the surfaces of the pores without actually condensing the vapour.

In some embodiments of the method the condensation kinetics of a gas are investigated by changing a temperature, to differentiate between different vapours which condense at different rates and to a different extent. The skilled person will appreciate that one waveguide may be operated at multiple different temperatures, changing the temperature of the waveguide in time and/or space (along the waveguide) and/or multiple different waveguides may be employed operating at multiple different temperatures.

In some embodiments of the method light of a single wavelength, for example from the light emitting diode or laser is waveguided to interrogate a particular target absorption (or scattering) peak or trough. In other approaches multiple substantially discrete wavelengths are employed, or broadband radiation may be employed, to measure an absorption (or scattering) spectrum. In particular, embodiments of the method measure an absorption (or scattering) spectrum of an analyte absorbed within the waveguide.

In embodiments the measured spectrum or interrogated wavelengths are characteristic of the analytes(s) under investigation rather than characteristic of the waveguide—that is the spectrum or wavelength(s) comprise an absorption (or scattering) spectrum or wavelength(s) of the analyte(s).

Depending upon how the waveguide is made, the pores may not have a well-defined size—for example where porous silicon is employed a surface of the silicon may have approximately regular pores whilst a vertical-cross section through the material may reveal a more fractal-like structure. Nonetheless it is possible to measure a pore size distribution and determine an average pore size, in particular at an outer surface of the core of the waveguide, as described later. When pore size is measured in this way the pores have a size distribution with a peak at less than 500 nm; or less than 400 nm, 300 nm, 200 nm, 100 nm or 50 nm. Alternatively the pore size may be specified as a mean, medium, mode or maximum dimension or pitch less than 500 nm; or less than 400 nm, 300 nm, 200 nm, 100 nm or 50 nm.

In embodiments the pores of the optical core may be substantially random or may have some (or substantially complete) regularity. For example in embodiments they may define an interconnected network; and/or they may, for example, define longitudinal passages. Whatever the change of the pores the light propagation through the pores themselves (rather than, say, through a region bounded by the pores). Where the pores have a generally longitudinal shape, the longitudinal axis may be aligned perpendicular to the direction of light propagation through the porous optical core.

In preferred embodiments of the method the pores are significantly smaller than a wavelength of the waveguided radiation, to reduce scattering losses in the waveguide. When measured at a surface of the core of porous material the pores may have an average minimum lateral dimension (measured on the surface) of less than 500 nm, 400 nm, 300 nm, 200 nm, 100 nm or 50 nm; or, for example, an average minimum lateral dimension at least two or preferably ten times smaller than a wavelength of the waveguided radiation.

If the average pore size (the average 'diameter' of a pore which extends longitudinally) in less than the wavelength(s) of light used then the porous material will be substantially transparent, or at least have reduced attenuation. In broad terms the light propagating through the porous material should not "see" a significant propagation (say more than 20%) of structure having a size greater than the wavelength(s).

Many different approaches may be employed to fabricate the porous core of the waveguide. These include, but are not limited to: electrochemical etching of semiconductors; a sol-gel process; nanoparticle self-assembly process; and use of porous alumina or porous polymers. In embodiments, however, the waveguide is fabricated on a substrate using porous silicon for the core (which may be oxidised to porous silica). Conveniently the substrate is silicon, although this is not essential as such a waveguide may be fabricated on silicon and afterwards lifted off.

In one approach the core material is separated from the underlying (silicon) substrate by a region of 'cladding', the cladding having a lower refractive index than the core (so that the core is separated from the higher refractive index silicon, to enable the waveguiding). In other approaches, however, the cladding is optional—for example a suitable waveguide may be fabricated from a layer of titanium dioxide (nano)particles which may be deposited directly on a non-porous substrate of lower refractive index, such as a silica surface. Thus in embodiments the core of a waveguide may be partially or completely surrounded by cladding (apart from a region exposing the core to gas/vapour), but this is not essential. Where cladding is present, it may be non-porous.

The skilled person will appreciate that in embodiments a substrate for the waveguide is not essential. It is useful in a layered structure, but in other arrangements the core (and optional cladding) may be suspended between supports, as illustrated schematically in FIG. 4c. This approach is particularly suitable for a fibre-type core but may also be used to support a slab of waveguide material (core with or without cladding). Supporting a waveguide comprising a porous core with an air or gas cladding is advantageous because it facilitates access of analyte to the porous material of the core. Thus in some approaches the core material may be separate from any substrate such that the surrounding environment, such as air, acts as a lower refractive index medium. This arrangement facilitates absorption of analytes into the core through the entire outer surface in a lateral direction.

In one approach a waveguide may be fabricated buried within the surface of a silicon substrate, by etching respective cladding and core layers into the surface of the silicon. In another, preferred approach however a waveguiding structure is supported on the surface of a silicon substrate.

Thus in a related aspect the invention provides a method of fabricating a waveguide for an analyte sensor as described above, the method comprising: providing a silicon substrate; supplying a first current at a first current density perpendicular to said substrate; performing a first etch of said substrate to fabricate said core layer; and supplying a second current at a second density slowly perpendicular to said substrate; performing a second etch of said substrate to fabricate said core layer.

Broadly speaking by applying a current in a vertical direction through a silicon substrate and then etching the substrate, for example using hydrofluoric acid, a porous layer can be grown down into the substrate. The current density determines the porosity. In this way a layered structure can be fabricated in which a core layer is disposed on a slightly more porous cladding layer of lower refractive index, which is in turn disposed on the underlying (silicon) substrate. Lateral edges of the core defining the waveguide may be formed either before or after the etching. The structure may then be provided with fibre optic input and output connections for waveguiding light through the structure.

In a related aspect the invention provides an analyte sensor, the sensor comprising: a substrate bearing a waveguide, the waveguide comprising: a first, cladding layer on said substrate; a second, (optical) core layer, comprising porous material, over said cladding layer; a radiation source to provide radiation into said waveguide; a radiation detector to detect radiation which has been waveguided along said waveguide; and a signal processor, coupled to said radiation detector, to identify the presence of a target analyte absorbed within said core layer from one or more spectral features of said detected radiation due to absorption or scattering of said waveguided radiation by said absorbed target analyte.

In embodiments of the above described sensor/method, an analyte fitter may be located above the core, in particular as an additional layer over the core (when it should have a lower refractive index than the core). For example, such a filter may comprise an additional layer of porous silicon over the core, optionally functionalised.

In a further related aspect the invention provides apparatus for selectively detecting the presence of an analyte, the apparatus comprising: at least one waveguide, the waveguide having (an optical) core comprising porous material; a radiation source to provide radiation into said waveguide; a radiation detector to detect radiation which has been waveguided along said waveguide; and a signal processor, coupled to said radiation detector, to identify the presence of a target analyte absorbed within said core layer from one or more spectral features of said detected radiation due to absorption or scattering of said waveguided radiation by said absorbed target analyte.

Corresponding features to those previously described may be provided in embodiments of the apparatus. Thus, for example, the signal processor may be configured to process signals from a plurality of core regions of the waveguide physically and/or chemically modified to be different to one another, to enhance the selectivity of the apparatus. Additionally or alternatively a temperature controller may be employed to operate one or more waveguides or portions of waveguides at different temperatures.

The skilled person will appreciate that the signal processor processing the signal from the radiation detector may comprise analogue or digital electronics and/or a processor, such as a digital signal processor or general purpose computer, operating under control of stored processor control code.

Embodiments of the above described methods and apparatus have many applications including, but not limited to: Detection of analytes that are toxic to human health and/or degrade air quality; detection of analytes in industrial chemical processes and reaction chambers; detection of analytes that constitute an explosive risk; detection of analytes that are associated with the detection of drugs/illegal substances; detection of analytes contained within human or animal bodily fluids (including for example exhaled breath, urine, blood, sputum); and detection of analytes from human or animal cell gas exchange.

One useful application is in analysing a urine sample, in particular to provide information on patient kidney function. The techniques we describe above are able to provide information which is difficult or impossible to obtain conveniently by other techniques. In particular the techniques we describe provide a sensitive, low cost method of obtaining an absorption spectrum of one or more, volatile organic compounds (VOCs) from the sample, especially VOCs associated with diseases such as kidney disease and cancers, such as colon cancer and prostate cancer.

In one embodiment apparatus for this purpose includes sensor apparatus as previously described, together with a urine sample holder and a shutter to selectively allow passage of urine vapour from the sample holder to the sensor for analysis.

BRIEF DESCRIPTION OF THE DRAWINGS

These and other aspects of the invention will now be further described, by way of example only, with reference to the accompanying figures in which.

DETAILED DESCRIPTION OF PREFERRED EMBODIMENTS

We will describe techniques for optical spectroscopy of analytes in the pores of a porous waveguide. Some initial background material is helpful for understanding the invention:

Spectroscopy

Optical absorption spectroscopy is based on illuminating a chemical compound with a light and measuring the light absorption as a result of a presence of that chemical compound. Different molecules absorb light of different wavelengths. An absorption spectrum will show a number of absorption bands corresponding to structural groups within the molecule.

Absorbance is directly proportional to the path length, b, and the concentration, c, of the absorbing species. Beer's Law states that A=εbc, where ε is a constant of proportionality, called the absorbtivity.

The radiation can be of any wavelength ranging from the UV to IR and even THz.

Porous Silicon

Porous silicon is typically fabricated using electrochemical etching. The porosity of the fabricated layer depends on several parameters (wafer doping, temp, solution) and the applied current density during the electrochemical etching. The refractive index of a porous layer depends on the porosity, and therefore can be easily controlled. This enables easy fabrication of optical components such as Bragg reflectors, multilayers structures and waveguides.

In addition, the porous nature of the material can be used to host other optical materials, nanoparticles, chemical molecules and dyes.

Waveguides

An optical waveguide is a physical structure that guides electromagnetic waves, i.e. the electromagnetic waves propagate within the boundaries of the structure. Optical waveguides can be classified according to their geometry (planar, strip, or fibre waveguides), mode structure (single-mode, multi-mode), refractive index distribution (step or gradient index) and material (glass, polymer, semiconductor). As the skilled person will appreciate, a waveguide generally comprises a core with a cladding (which may be gas/air/vacuum) of lower refractive index.

Capillary Condensation

The number of molecules that can be adsorbed by a porous layer is limited by the total pore volume. The pores' curved surfaces enhance the attraction for molecules of wetting substances due to van der Waals interactions, resulting in adsorption and capillary condensation. Capillary condensation is the physical tendency for a vapour to condense in a small pore at temperatures well above the dew point, and is described by the Kelvin equation:

$$N_A kT \ln\left(\frac{P}{P_0}\right) = -\frac{2M\gamma \cos\theta}{r\rho}$$

where $N_A$ is Avogadro's constant, k is the Boltzmann constant, T is the absolute temperature, M is the molecular weight, $\rho$ is the liquid density, r is the radius of the capillary, $\theta$ is the contact angle, $\gamma$ is the surface tension, $P_0$ is the saturation pressure and P is the equilibrium vapour pressure. Therefore, the smaller the pore radius, the lower is the relative vapour pressure at which capillary-condensation can occur at a given temperature. During the capillary-condensation process, the air in the voids is replaced by condensed vapour. The extent of both the monolayer adsorption and the capillary condensation are influenced by the surface affinity of the porous matrix, which can be tailored by a range of chemical modifications.

Thermal Modulation

For a single sensor, using thermal modulation, can help discriminate between different vapours. When the sensor working temperature is modulated, the kinetics of the adsorption and reaction processes that occur on the sensor surface are altered. This leads to sensor response that is characteristic to species present, thus increased selectivity.

Porous Waveguide Sensing

Embodiments of the invention relate to the use of a porous waveguide with sub-wavelengths features with a light source and detector to measure molecular absorption spectroscopy of species entering the pores of the waveguide. The porous waveguide can be made of any material and may be fabricated in many different ways. Pore and nano-features dimensions are smaller than the wavelength of light, where Rayleigh scattering losses (which vary as $\lambda^{-4}$) are expected to be low enough to allow light to propagate in the waveguide. The preferred waveguide design we describe facilitates easy access of analytes into the pores (by contrast with 'buried' waveguides made of porous silicon). The detection optionally employs the capillary condensation phenomenon to facilitate further discrimination of analytes that enter the pores.

Current optical (bio-)sensors are limited in their sensitivity because the chemical interactions are limited to the surface of the waveguiding device, while the high-intensity propagating mode is localised in the core. Increasing the interaction between the propagating light and the target molecules, as well as increasing the surface area, results in increased sensitivity and better SNR.

Figure 1:
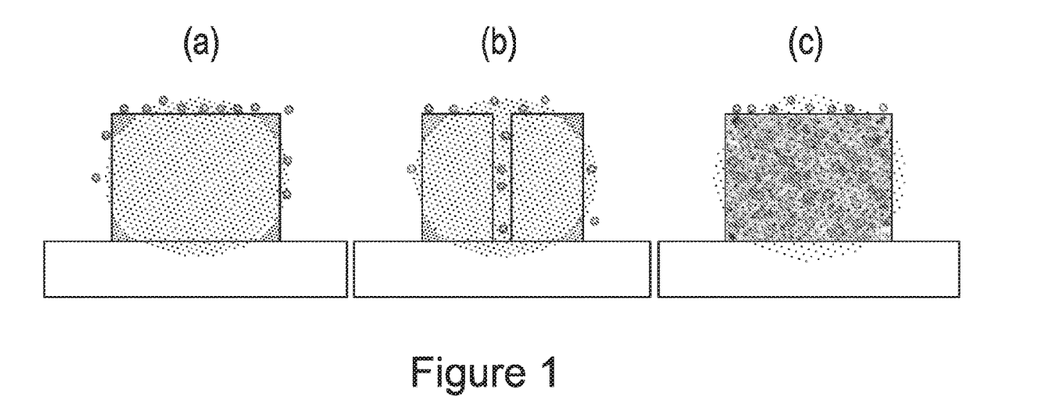
FIG. 1 shows a schematic illustration of three different waveguide types and their interactions with molecules, showing (a) a conventional waveguide, (b) a slot-waveguide and (c) a porous waveguide according to an embodiment of the invention; the target analyte molecules are represented as dots and the diffuse circles represent the propagating mode.

In FIG. 1, three different types of waveguides are compared. FIG. 1a shows a conventional waveguide where the light propagates in the core and only the evanescent field interacts with the molecules of interest (dots). One way to improve the sensitivity is to add a small slot inside the core (FIG. 1b). This slot is very thin (smaller than the wavelength of light) in order for the mode to propagate 'normally' in the structure. This adds to the complexity of fabrication, and also the slot is limited in the number of molecules that it can accommodate. A porous waveguide (FIG. 1c) comprises many small pores, with the ability to accommodate large quantity of molecules. The target molecules are absorbed within the waveguide core, thus providing very sensitive detection. Due to the small size of the pores (much smaller than the wavelength of light), the light can propagate in the porous core in a similar manner to a conventional waveguide.

In addition to the large surface area which is generally desirable by a sensor, the porous network offers additional advantages: The size of the pores can be tuned. This can provide physical discrimination based on size—for example only the smaller molecules may be measured. The surface may be treated to become hydrophilic, hydrophobic or may be tailored by a range of chemical modifications. The surface may be functionalized with receptors to allow specific binding with the target molecules (DNA, antibody).

Figure 2:
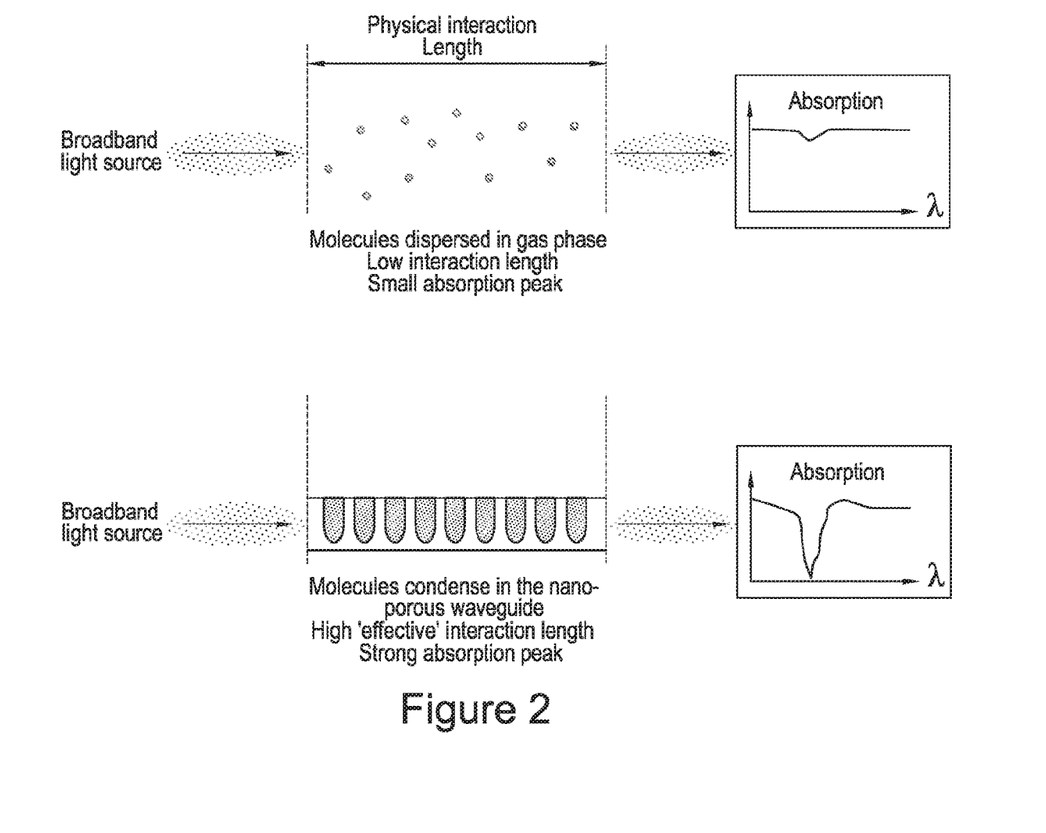
FIG. 2 illustrates absorption of light by molecules, showing that for the same physical interaction length, a nanoporous waveguide (lower figure; dispersed molecules, small interaction length, small absorption peak) provides significantly higher effective interaction length than with a gas (upper figure; molecules condensed within the material of the waveguide core, large effective interaction length, strong absorption peak), thus increasing the sensitivity of detection.

In the gas phase, the nanostructured optical waveguide significantly increases the sensitivity of detection for volatile organic compounds (VOCs) due to a capillary condensation phenomenon: Capillary condensation is the physical tendency for a vapour to condense in a small pore at temperatures well above the dew point (as described by the Kelvin equation). During the capillary-condensation process, the air in the voids is replaced by condensed vapour. The extent of the condensation is influenced by the surface affinity of the porous matrix to the vapour molecules and depends on the vapour intrinsic properties. The molecules in the liquid are in equilibrium with the gaseous molecules, and the process is reversible: as the gas concentration decreases, the molecules leave the pores. The nanostructured optical waveguide acts as a condenser or concentrator of organic volatiles. FIG. 2 is a schematic illustration showing the role of the nanostructured waveguide: Conventionally, the light interacts with gas molecules which are dispersed in air. However when a nano-porous waveguide is introduced, the gas molecules condense inside the waveguide, providing a significantly larger effective interaction length.

Figure 3:
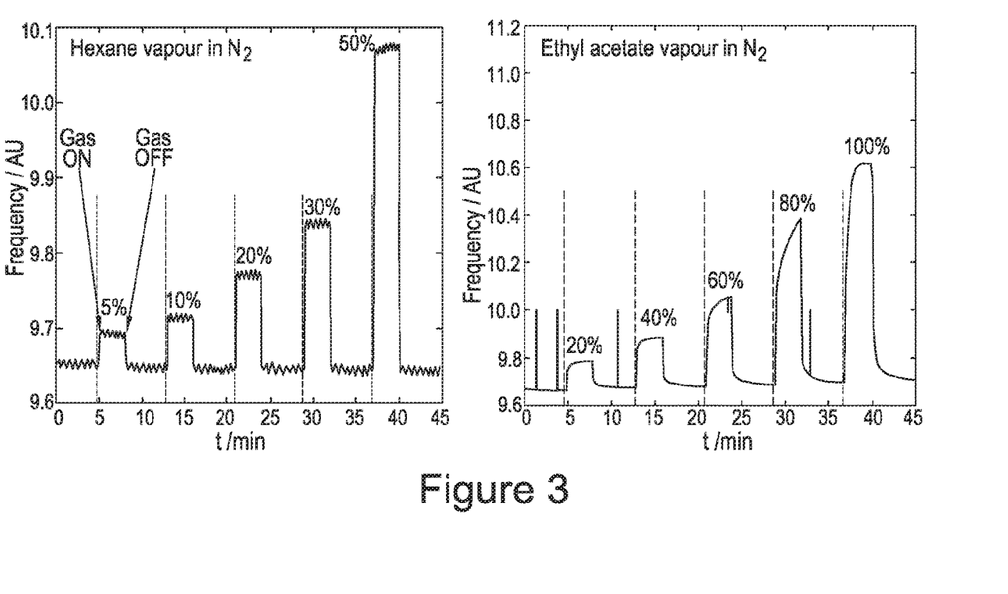
FIG. 3 shows the dynamic response of a single porous silicon layer for hexane vapour (left) and ethyl acetate vapour (right) at various concentrations, showing a measure of physical absorption of the vapour by the porous silicon on the y-axis.

The dynamic curves of adsorption, condensation and desorption are different for different vapours. FIG. 3 shows the real-time sensor response for 5 injections of two different vapours. The adsorption and desorption of vapour into and out of the porous structure is fast and fully reversible (albeit with some hysteresis).

We now describe some further methods of improving the reliability and the selectivity of this approach: Temperature modulation provides further discrimination—the capillary condensation and thus the dynamic curves are different for different vapours. A waveguide array, in particular an array of waveguides having different pore sizes and/or surface treatment or surface functionalization facilitates discrimination between target analytes. These techniques facilitate discrimination based on analyte size and/or mass and/or boiling point, and discrimination between structural isomers and functional groups.

Initial feasibility tests were successfully conducted using the structure of FIG. 4, which illustrates a fabricated waveguide. To make the waveguide samples were prepared using p-type doped silicon substrates with a resistivity of 0.01 Ω-cm and (100) crystal orientation. The grooves (1.2 μm high and 70 μm wide) for the waveguides were etched using standard lithographic process, and then the pores were etched electrochemically using an electrolyte solution containing 30% HF (48% aqueous) and 70% ethanol. The thickness of the core and cladding layers were 3 μm each. As the refractive index is determined by the applied current density, it is possible to design multi-layered structures and graded-index planar waveguides in which the porosity is varied through the vertical cross section of the structure.

Figure 4A:
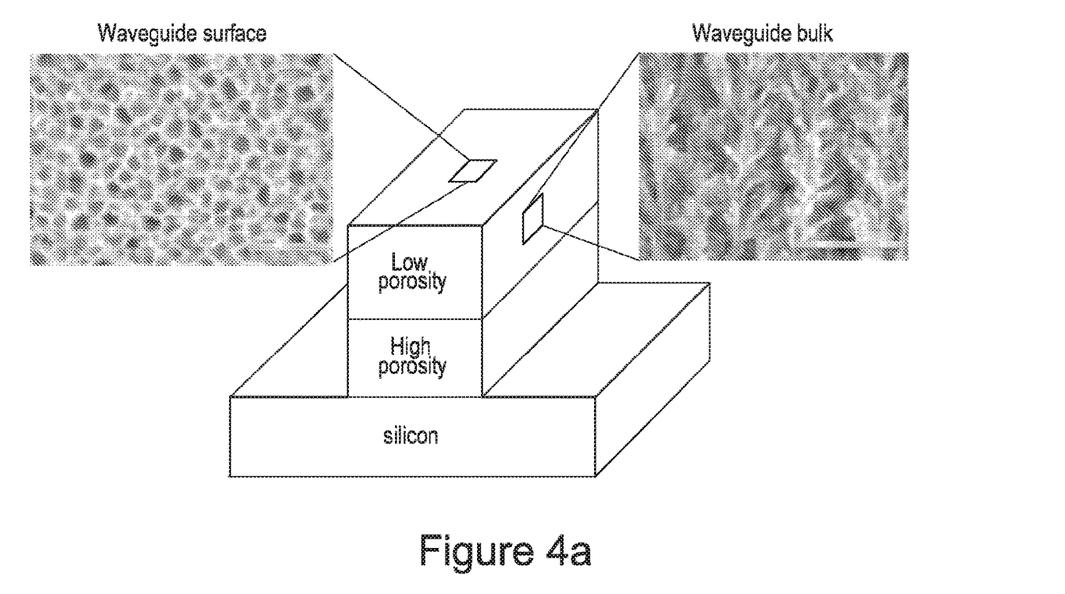
FIGS. 4a to 4c show, respectively, the structure of an example fabricated PSi (porous silicon) waveguide comprising a porous core layer on a cladding layer, with inset HR-SEM (high resolution scanning electron microscope) images of the top surface and a cross-section view of the pore morphology (the scale bars are 100 nm); a first variant waveguide structure; and second variant waveguide structure without substrate or cladding.
Figure 4B:
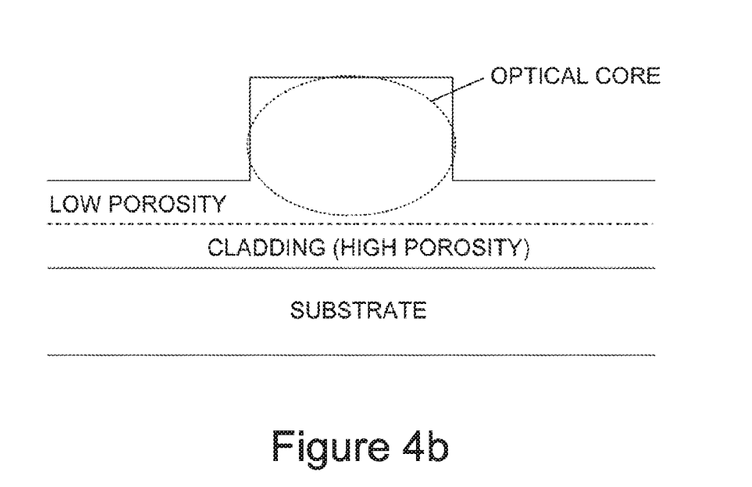
Figure 4C:
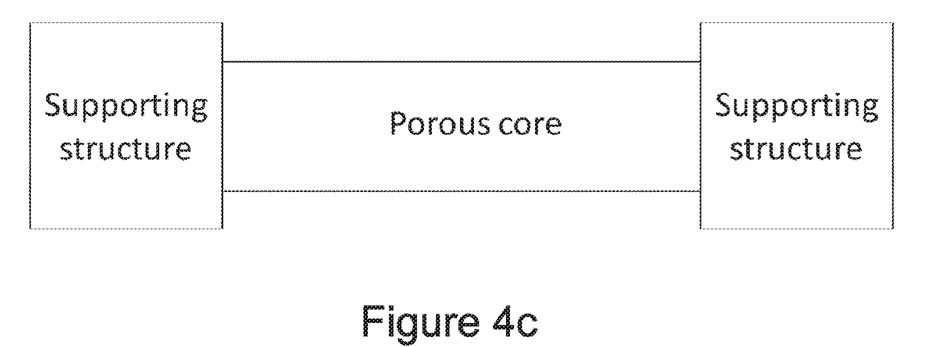

The structure of an example resulting waveguide is shown in FIG. 4a, with the top view and the cross-section morphology of porous silicon. The upper core is a low porosity layer and the cladding is a high porosity layer. Alternatively a waveguide may be fabricated with an extended low porosity layer with a raised optical (core) region in which light propagates, as illustrated in FIG. 4b.

Figure 5A:
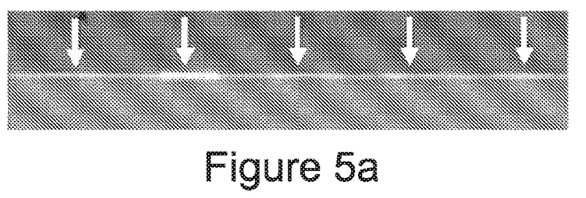
FIGS. 5a to 5c show a vertical cross-section of a porous waveguide array (individual waveguides indicated with arrows), showing the emitted light from two adjacent waveguides (FIGS. 5a, 5b), and light propagation along a waveguide (FIG. 5c)
Figure 5B:
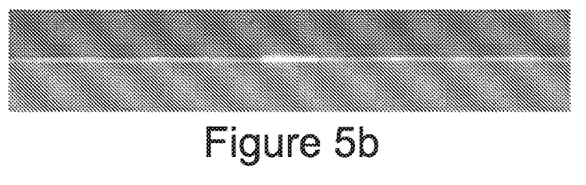
Figure 5C:
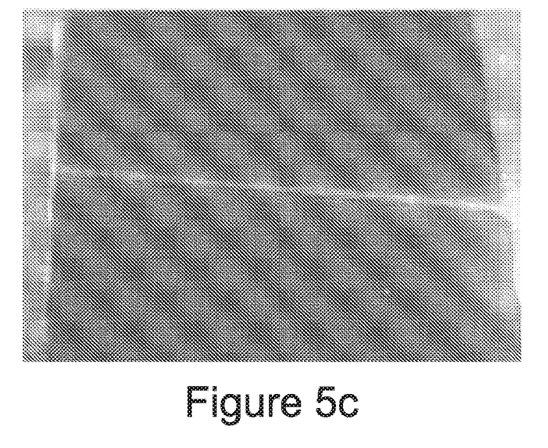

FIGS. 5a and 5b show a vertical cross-section (end-on) view of a waveguide array fabricated in this manner. FIG. 5a shows light coming out of a second waveguide of the array; FIG. 5b shows light coming out of a third waveguide of the array. FIG. 5c shows a view from above of light propagation in one of the waveguides of the array.

Figure 6:
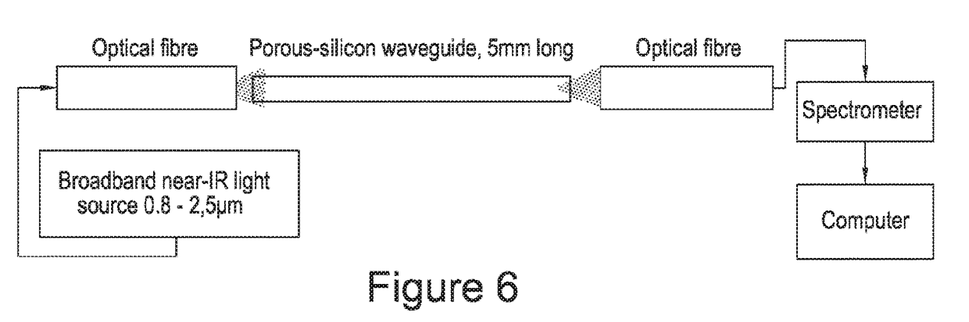
FIG. 6 shows, schematically, experimental apparatus used to characterise a sensor according to an embodiment of the invention.
Figure 7A:
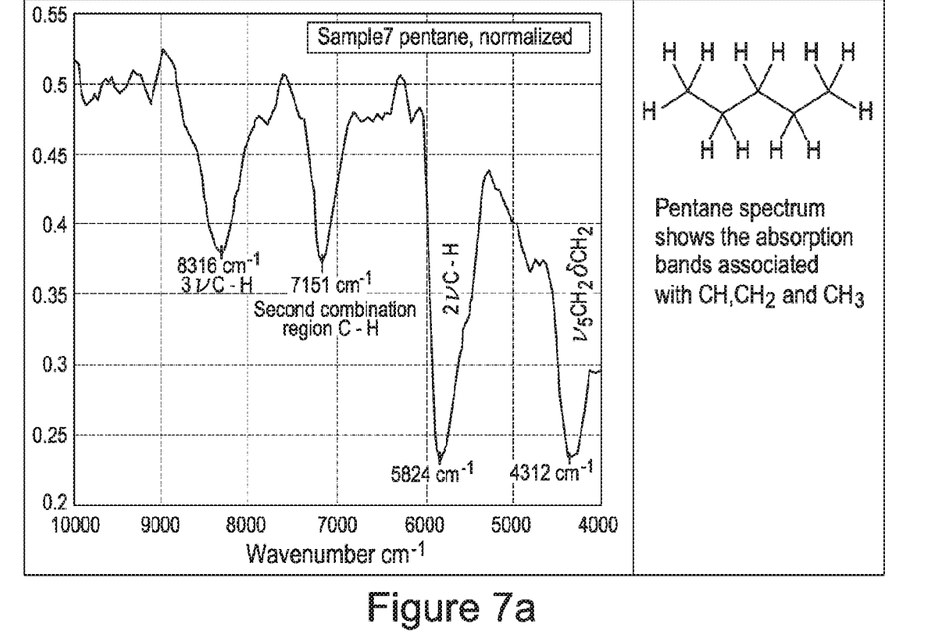
FIGS. 7a to 7d show example measured spectra from the apparatus of FIG. 6 for, respectively, pentane, methanol, acetone and isopropyl alcohol.
Figure 7B:
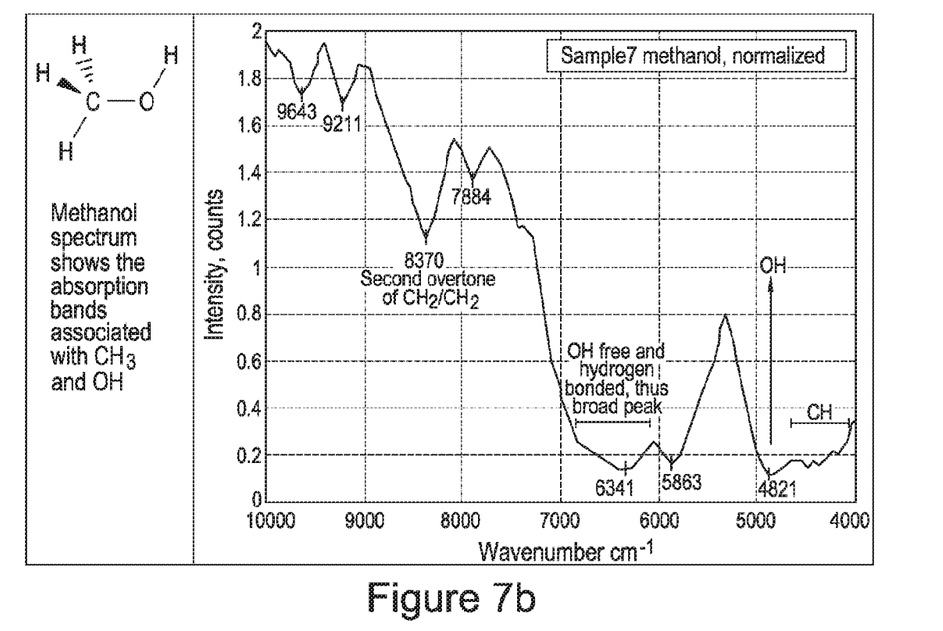
Figure 7C:
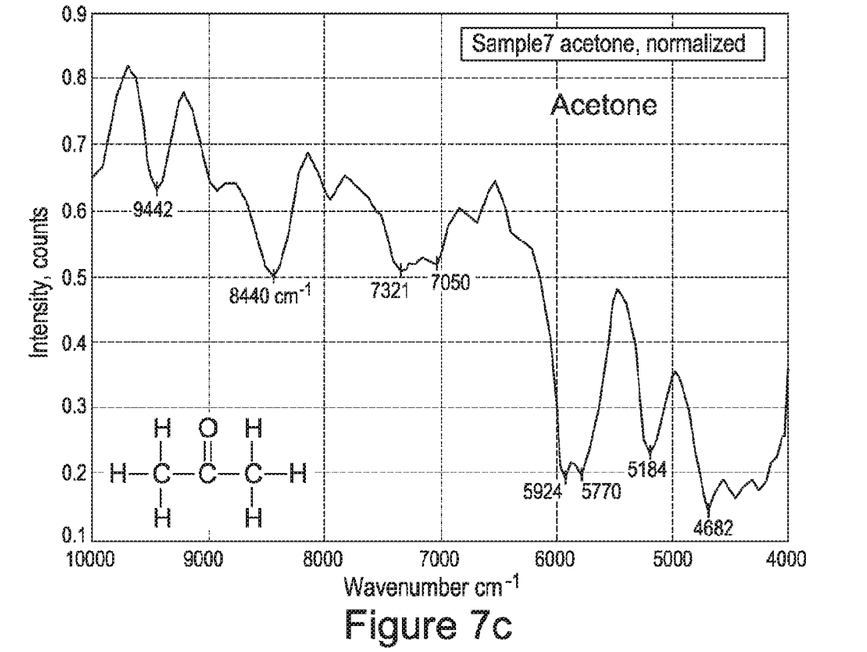
Figure 7D:
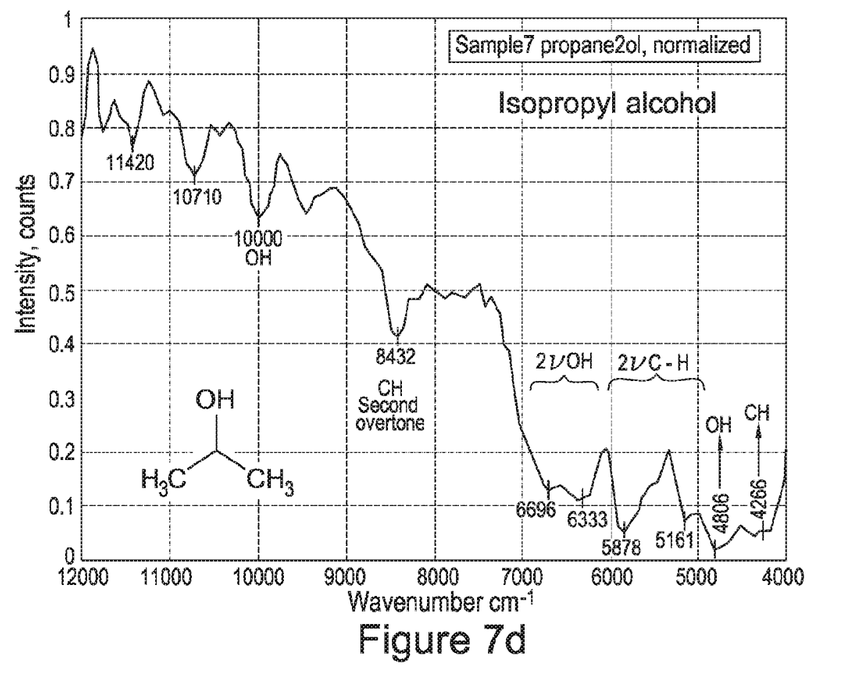

FIG. 6 shows an experimental setup used to carry out near-IR measurements with the porous silicon waveguide. A small tube carrying saturated vapours of different solvents (pentane, methanol, acetone and isopropyl alcohol) was placed above the waveguide in open air. The optical spectrum was then immediately recorded. The measured spectra are shown in FIG. 7.

As-prepared porous silicon is optically transparent from about 1 μm. To facilitate use in the visible, thermal oxidation can be employed to transforms silicon to silica, resulting in porous silica waveguides which are transparent at visible wavelengths and up to about 2.5 μm.

In embodiments of the invention the pore size of the waveguide core typically has a size in the range 5 nm-30 nm. More generally, however, the pore size may lie in a range of from <1 nm up to a size that is smaller than the wavelength used, for example up to 500 nm.

The pore size is preferably measured at the surface of the core of the waveguide for example by AFM (atomic force microscopy) or SEM. This is because in embodiments the pores do not have a well-defined size within the bulk of the material (FIG. 4).

The pore size of an individual pore may thus be taken as the average diameter of a pore or the average width of the pore (for non-spherical pores). The pore size of all pores will have a range or distribution of values; the pore size may be taken as the peak of this distribution (the mode of the pore size).

Other methods to measure porosity and pore size distribution include gas adsorption isotherms of N2 or CO2 at low temperatures. From those, the porosity and pore sizes may be calculated (indirectly), with some assumptions. For example, a pore size distribution may be calculated using the BJH (Barrett-Joyner-Halenda) method, which determines a pore size distribution based on a model of the adsorbent as a collection of cylindrical pores (Barrett, E. P.; L. G. Joyner, P. P. Halenda (1951), "The Determination of Pore Volume and Area Distributions in Porous Substances—Computations from Nitrogen Isotherms". *J. Am. Chem. Soc.* 73 (1): 373-380).

Alternatively, however, the porosity (proportion of total pore volume in a material) may be used as a proxy for pore size. This may be determined using a gravimetric method, as described in "*Porous Silicon in Practice*", Prof. Michael J Sailor, Wiley-VCH, 2012, at page 134. Broadly speaking, this etches away a known volume of silicon, weighs the silicon before and after, and calculates the actual volume of silicon removed from the density of silicon, giving the percentage porosity. In some preferred embodiments of the techniques we describe the porosity of the waveguide core may be in the range 10% to 90% porosity, preferably the waveguide core has >40% porosity (the cladding, where present has a higher porosity than the core).

Figure 8A:
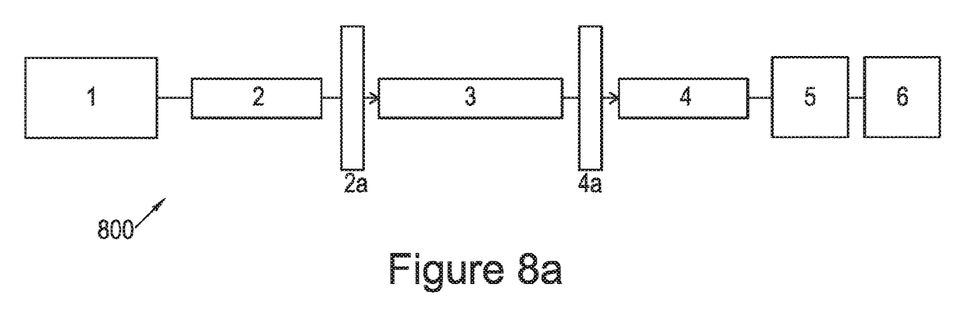
FIGS. 8a to 8d show analyte sensing systems according to embodiments of the invention.

FIG. 8a shows an analyte sensing system 800 according to an embodiment of the invention. The system comprises an optical source 1 such as an LED, laser or lamp coupled to an optical fibre 2 and optional filter 2a to provide an optical input to a porous waveguide sensor 3 as previously described. Light output from porous waveguide 3 optionally passes through a second filter 4a into a second optical fibre 4 to an optical detector 5 such as a photodetector or spectrometer. The signal output from detector 5 provides an input to a signal processor 6 such as a suitably programmed general purpose computer or dedicated signal processing circuitry.

Figure 8B:
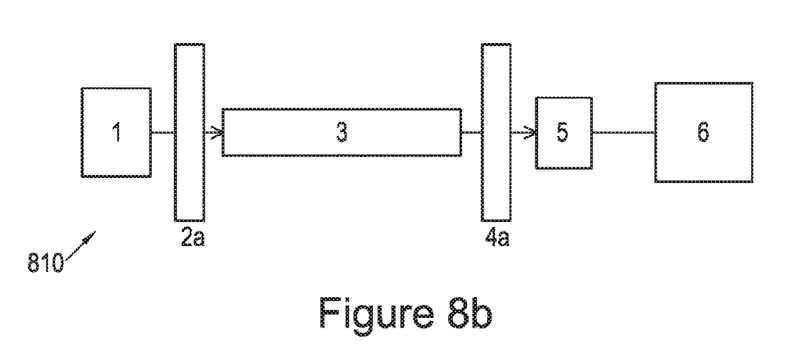

Referring now to FIG. 8b, this shows a second analyte sensing system 810, similar to that of FIG. 8a, in which optical fibres 2 and 4 are omitted. The optional filter 2a and optional filter 4a may comprise a narrow passband optical filter such as an interference filter or a multiple passband filter, for example aligned to one or more absorption peaks of a target analyte.

Figure 8C:
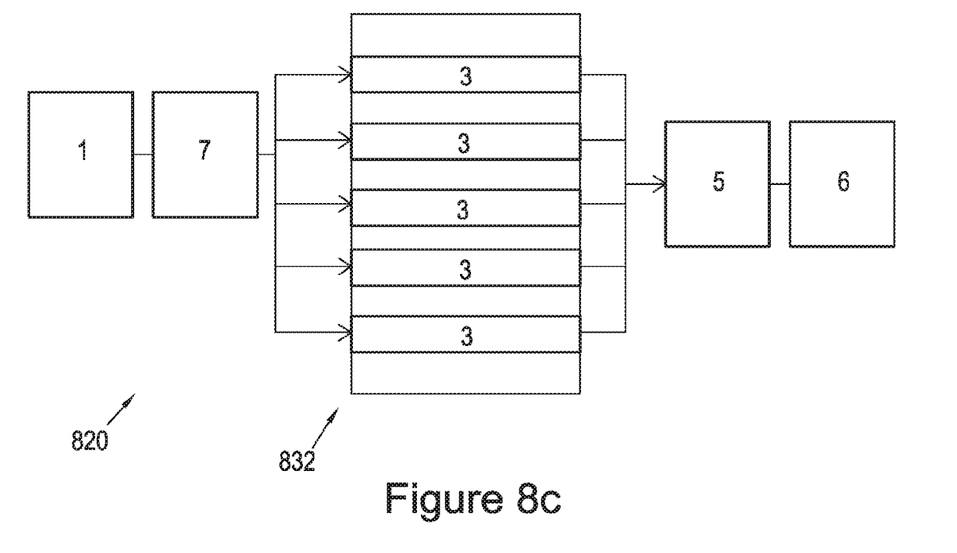
Figure 8D:
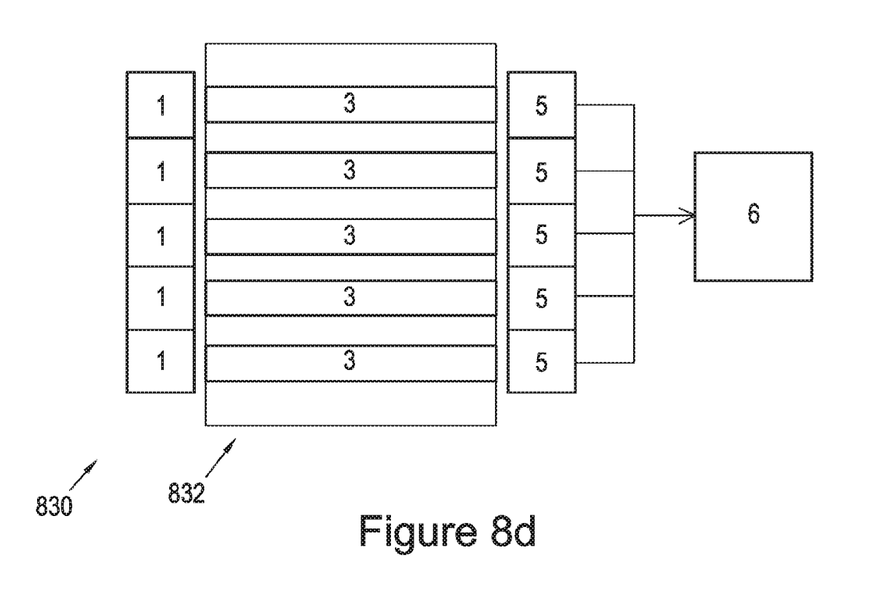

FIG. 8c shows a waveguide array analyte sensor 830 in which like elements to those previously described are indicated by like reference numerals. Thus the sensor system 830 comprises an optical spatial multiplexer 7 to distribute light from source 1 into each of a plurality of waveguides 3 arranged as a waveguide array 832. In FIG. 8c the outputs of waveguides 3 are combined, optionally by an optical combiner (not shown). As illustrated in the variant waveguide array sensor system 840 of FIG. 8d, one or both of the optical source(s) one and optical detector(s) 5 may be replaced by a plurality of sources/detectors rather than multiplexed.

Figure 9:
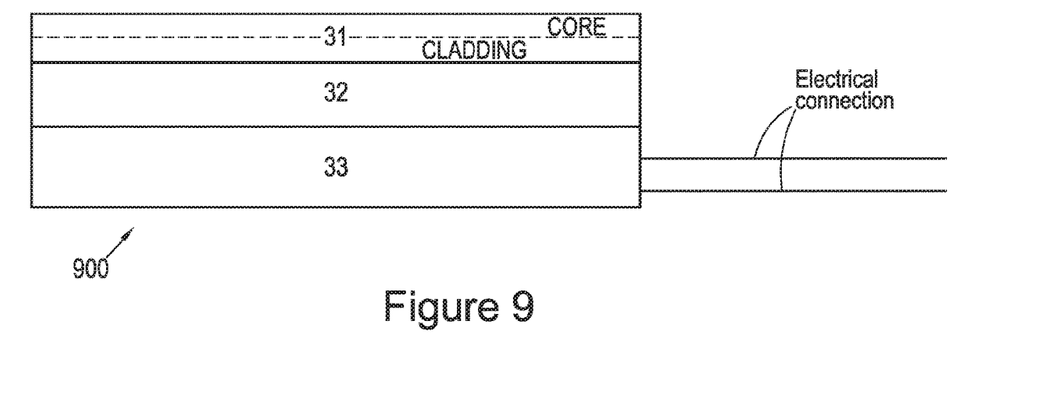
FIG. 9 shows a vertical cross-section through a temperature controlled porous waveguide sensor according to an embodiment of the invention.

FIG. 9 illustrates a temperature controlled porous waveguide 900 for use in any of the sensor systems of FIG. 8. The porous waveguide 900 comprises a substrate 32 bearing a porous waveguide 31, for example comprising a core layer over a lower refractive index cladding layer. A heating element 33 is provided under substrate 32, for example comprising a heating element and/or Peltier effect device, preferably with a temperature sensor for closed loop temperature control of substrate 32 and waveguide 31.

Figure 10:
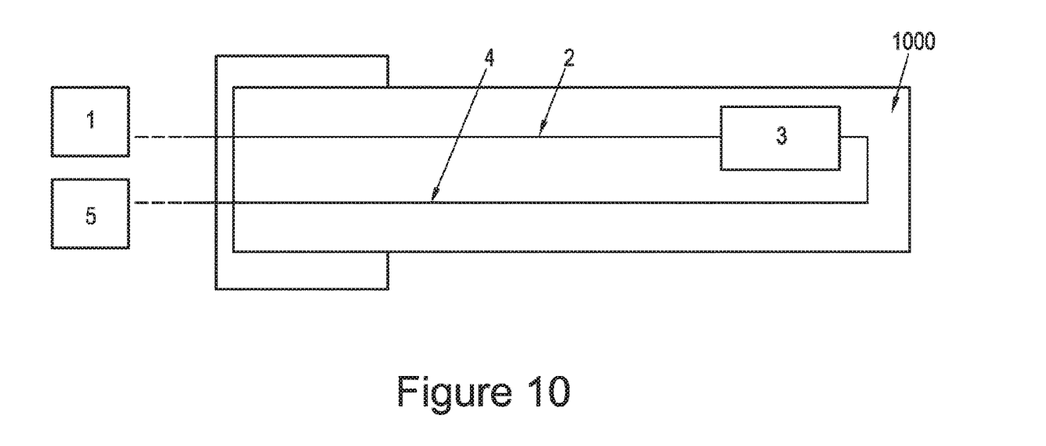
FIG. 10 shows an example of an analyte sensing probe comprising a porous waveguide according to an embodiment of the invention.

FIG. 10 shows an embodiment of a sensor probe 10 comprising a porous waveguide sensor 3 as previously described. Fibre optic connections 2, 4 provide respective input and output connections for the porous waveguide sensor, and these are respectively coupled to a remote optical source 1 and to a remote optical detector 5.

Thus, broadly speaking we have described a sensor device for measuring molecular absorption or Raman spectroscopy of analytes, the device comprising a light source, a porous waveguide and a detector. Here molecular spectroscopy refers particularly to UV, near-IR, mid-IR and far-IR absorption bands of analytes that enter into (are absorbed by) the material of which the porous waveguide is fabricated.

In embodiments the porous waveguide may be made of silicon, silica, alumina, chalcogenide, titanium dioxide or other materials that are transparent or partially transparent in the desired optical range. Typical dimensions for the porous waveguide have width and height on a micrometre scale, a length in millimetres, and the inner, pore features smaller than the wavelength of light.

The light source used may provide one or more wavelengths in the range of UV, near-IR, mid-IR and far-IR. The source may be either a broad light source or provide a one or more specific wavelengths. The detector may be, for example, a spectrometer or a photo-detector with or without an optical filter. Where used, a filter can be put at the light source and/or at the detector.

Optionally the external and/or internal surface of the porous waveguide (i.e. the outer face and/or the surface within the pores) may be chemically treated to be either hydrophilic, hydrophobic or functionalised with various chemical groups. Thus the surface may be functionalised with receptor molecules such as DNA, protein, or antibody molecules.

Embodiments of the sensor may be used to sense an analyte in either the gas or liquid phase.

In the gas phase, different vapour-phase materials, for example VOCs (volatile organic compounds), will condense differently inside the pores (according to the Kelvin equation). The adsorption and desorption of the gases into and from the pores, may be monitored in real-time to provide time-dependent information.

The diffusion of analyte into the core, retention of analyte within the core, and analyte condensation is temperature-sensitive. Therefore embodiments comprise a heater plate attached, for example, to the back side of the waveguide. By controlling the temperature one can tune which analytes, for example VOCs, will condense inside the pores, and which will not (or at least which preferentially condense/do not condense). Optionally temperature modulation may be employed in order to obtain a time-dependent temperature data for further discrimination.

Embodiments of the sensor system may in particular be used to measure gaseous analytes emitted from breath, urine or other biological/human solids, bodily fluids or vapours.

The sensor or a similar device may also be used to 'hold' analyte as a condensed vapour—by allowing the analyte to enter the core and then lowering the temperature to condense the analyte. The "stored" gas (vapour) may be released by increasing the temperature.

In addition to the light transmission through the waveguide, embodiments of the sensor system also (optionally simultaneously) monitor the change in the refractive index of the waveguide, for example via white light reflection.

Additionally or alternatively one or more dc or ac electrical properties of the sensor (waveguide) core may also be monitored, for example resistivity/conductance, and/or impedance. For example a pair of electrodes may be located on (along) the low porosity or core part of the waveguide and connected to an electrical characterisation device/system, for example for measuring resistance, impedance and/or dielectric constant. In a device of the type shown in FIG. 4b the electrodes may be located alongside the core on the low porosity material, for ease of fabrication.

Such refractive index/electrical data may be used for sensing/discriminating between analytes.

Optionally the device may have one or more waveguides in parallel. In embodiments each waveguide has different surface chemistry, porosity, temperature, and/or other features. This arrangement can improve the sensitivity/selectivity of the sensor system, by combining the data from the sensor array.

Embodiments of the waveguide may be fabricated in many ways. For example porous silicon may be produced by electrochemical etching. Optionally a porous silicon waveguide layer (core and optional cladding layer) may be removed from the substrate after fabrication and placed on a substrate other than silicon.

In another method nanoparticles are deposited on a substrate to create a porous layer. In addition there are many methods which may be employed to exist to produce a porous material using a sol-gel process. Optionally one or more sensitising/functionalising molecules/nanoparticles may be incorporated inside the porous media. These may be employed to tune the optical and/or chemical properties for sensing. Optionally a gain material (a material for providing optical gain) may be incorporated within the waveguide, either distributed within the waveguide or in one or more discrete regions.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method of selectively detecting the presence of an analyte, the method comprising:
providing at least one waveguide, the waveguide having a core comprising porous material;
absorbing an analyte sample into said porous material of said core such that said analyte sample is held within pores of said core;
waveguiding radiation along said at least one waveguide to an output to provide output radiation;
measuring one or more spectral features of said absorbed analyte sample in said output radiation due to absorption of said waveguided radiation by said absorbed analyte sample;
selectively identifying the presence of a target analyte in said analyte sample from said one or more spectral features;
wherein an average lateral dimension of the pores in said core of porous material is at least ten times smaller than a wavelength of the waveguided radiation; and
wherein molecular absorption spectroscopy is performed on said analyte sample.

2. The method of claim 1, wherein said one or more spectral features are enhanced by capillary condensation.

3. The method of claim 1, further comprising providing a plurality of waveguide core regions with a plurality of different physical and/or chemical modifications to said core, wherein said plurality of waveguide core regions comprise one or both of a plurality of core regions of a plurality of said waveguides and a plurality of core regions of a plurality of portions of said at least one waveguide;
waveguiding radiation through said plurality of waveguide core regions;
measuring one or more said spectral features for each of said differently modified core regions; and
selectively identifying said target analyte from a combination of said spectral features for said differently modified core regions.

4. The method of claim 3, wherein said differently modified core regions have pores with size distributions having peaks at different pore sizes.

5. The method of claim 3, wherein said differently modified on regions comprise different functionalizations of said core material.

6. The method of claim 3, wherein said selective identifying uses a multi-component analysis of said combination of spectral features.

7. The method of claim 1, further comprising operating at a plurality of temperatures of said at least one waveguide, and measuring said one or more spectral features at said plurality of temperatures; wherein said selective identifying is responsive to said one or more spectral features at said plurality of temperatures.

8. The method of claim 7, wherein said temperatures are selected to change a degree of vapor condensation of said target analyte within said pores of said core.

9. The method of claim 1, wherein said measuring comprises waveguiding multiband radiation along said waveguide and measuring a spectrum of said output radiation.

10. The method of claim 1, wherein said pores have a size distribution with a peak at less than 500 nm.

11. The method of claim 1, comprising providing said waveguide on a substrate and using porous silicon or porous silica for said core.

12. A method of analyzing a bodily fluid sample using the method of claim 1.

13. The method of claim 1, further comprising providing the waveguide with a cladding layer, wherein the cladding layer has a higher porosity than the core.

* * * * *